US011421257B2

(12) United States Patent
Farrell et al.

(10) Patent No.: US 11,421,257 B2
(45) Date of Patent: Aug. 23, 2022

(54) PROCESS FOR PRODUCTION OF SUGAR FROM A COTTON-CONTAINING TEXTILE

(71) Applicant: Cotton Incorporated, Cary, NC (US)

(72) Inventors: Matthew J Farrell, Apex, NC (US); Sha Fu, Garner, NC (US); Mary A Ankeny, Raleigh, NC (US)

(73) Assignee: Cotton Inc., Cary, NC (US)

( * ) Notice: Subject to any disclaimer, the term of this patent is extended or adjusted under 35 U.S.C. 154(b) by 0 days.

(21) Appl. No.: 16/914,013

(22) Filed: Jun. 26, 2020

(65) Prior Publication Data

US 2021/0002683 A1 Jan. 7, 2021

Related U.S. Application Data

(60) Provisional application No. 62/869,485, filed on Jul. 1, 2019.

(51) Int. Cl.
  *C12P 19/16* (2006.01)
  *C12P 19/02* (2006.01)
  *C12P 7/10* (2006.01)

(52) U.S. Cl.
  CPC .................. *C12P 19/02* (2013.01); *C12P 7/10* (2013.01)

(58) Field of Classification Search
  CPC ........................................................ C12P 7/10
  See application file for complete search history.

(56) References Cited

U.S. PATENT DOCUMENTS

| 10,611,891 B2 | 4/2020 | Hu et al. |
| 2011/0209387 A1 | 9/2011 | Humphreys |
| 2011/0236945 A1 | 9/2011 | Barbier et al. |
| 2013/0143277 A1 | 6/2013 | Gutierrez et al. |

FOREIGN PATENT DOCUMENTS

| CN | 102911395 A | 2/2013 |
| WO | 2019094444 A1 | 5/2019 |

OTHER PUBLICATIONS

Kuo et al., BioResources, 9(2), 2866-2875, 2014.*
Azam Jeihanipour and Mohammad J. Taherzadeh, "Ethanol production from cotton-based waste textiles," Bioresource technology, (2009), vol. 100, No. 2: 1007-1010.
International Search Report for Application No. PCT/US2020/039954 dated Sep. 25, 2020.
International Preliminary Report on Patentability for International Patent Application No. PCT/US2020/039954 dated Jan. 13, 2022.

* cited by examiner

*Primary Examiner* — Maryam Monshipouri
(74) *Attorney, Agent, or Firm* — McBee Moore & Vanik IP, LLC; Susan McBee; Christopher Nichols

(57) ABSTRACT

Cotton-containing textiles, such as "trash" feedstock in terms of end-of-life-cotton textiles, may be used to produce sugar without the same kinds of harsh pretreatments used for other biomasses, such as corn, grass sources, or wood. Disclosed is a process for production of sugar from a cotton-containing textile waste fabric comprising optionally mechanically pretreating the cotton-containing textile, pretreating the cotton-containing textile with an acid pretreatment to form a slurry, cooling the slurry, adding at least one base to the slurry, adding at least one additional acid to the slurry to form a buffer in situ, adding a hydrolysis enzyme, and optionally filtering the slurry.

16 Claims, 3 Drawing Sheets
(1 of 3 Drawing Sheet(s) Filed in Color)

PROCESS FOR PRODUCTION OF SUGAR FROM A COTTON-CONTAINING TEXTILE

CROSS-REFERENCE TO RELATED APPLICATIONS

This application claims the benefit of U.S. Provisional Application No. 62/869,485, filed on 1 Jul. 2019, which is incorporated by reference in its entirety.

FIELD OF THE INVENTION

This disclosure relates to a process for producing sugar from cotton-containing textiles.

BACKGROUND OF THE INVENTION

Biomasses are bio-derived feedstocks utilized to typically make sugar or other value added products that in turn can be utilized in many chemical or physical processes. Typically, biomasses must be pretreated first to open the protective shell around the cellulose to allow an enzyme to penetrate the biomass and start to hydrolyze the cellulose or starch chains. There exists already an industry producing cellulosic and starch ethanol that comes from biomass such as corn, grass sources, or wood. These biomass sources require land to grow, and the amount of sugar obtained is much lower than cotton textiles. Additionally, such sources (or feedstock) typically require harsh pretreatments to obtain the sugars from these sources. The use of such harsh pretreatments, in turn, requires rinsing and neutralization of the feedstock.

Because of the aggressive pretreatment required for cotton (plant, stalk, fibers etc.), cotton has not really been considered as a high value biomass feedstock. Additionally, cotton typically has a higher degree of crystallinity that makes bioconversion even more challenging. However, cotton in the form of textiles is 90+% pure cellulose and subsequently glucose that has already been processed and, if at the end of life of the consumer good, is essentially a free feedstock for bioprocessing. If end-of-life cotton garments are utilized instead of biomass grown for use as a feedstock, an environmental benefit is obtained, in addition to economic benefits, as long as the process is not cost prohibitive.

Textile cotton or recycled textile cotton is defined as a collected raw material (clothing at the end of its service life, scraps of fabrics from the garment industry, dust, etc.) that is a waste and the cotton component by nature is composed of more than 90% cellulose (which can be converted into sugar).

A use of textile cotton for producing ethanol is known from the publication "Ethanol Production from Cotton-Based Waste Textiles" (JEIHANIPOUR AND TAHERZA-DEH MJ, BIORESOURCES TECHNOLOGY, Vol. 100, No. 2, published online on Aug. 23, 2008). However, the process that is described, which provides in particular a chemical pretreatment stage, is not satisfactory in terms of yield and requires the use of concentrated products, which makes it not very economical and difficult to produce on the industrial scale. Additionally, the process of Jeihanipour found that alkali pretreatment applied to cotton waste was more effective than acid pretreatment. Finally, although the application of alkali pretreatment at lower temperature (−20-0° C.) enhances hydrolysis efficiency, it may be impractical to facilitate in a production facility.

Similarly, it has been suggested to use concentrated N-methylmorpholine-N-oxide (NMMO) as a solvent for the pretreatment of cotton textile waste fabric to disrupt the highly crystalline cellulose polymeric network. Although the NMMO pretreatment has been found to be effective, employing the pretreatment is costly due to the expense of NMMO and extensive process steps required.

Traditionally, the cost of sugar from cellulose has been high, so it has been slow to develop and commercialize. For production of sugar from cotton textiles, it has been suggested to use exotic solvents, high levels of acids, or high levels of caustic at low temperatures. However, these suggestions are not realistic solutions due to cost and additional materials needed to neutralize high levels of acid or caustic, recovering and recycling solvents along with the costs of the solvents, and for caustic, maintaining a temperature near freezing. In addition to neutralizing the acid or caustic, the neutralized component needs further to be rinsed.

There exists therefore the need for a lower-cost, less-harsh method for producing sugar suitable for production of ethanol or other value added products from cotton textile waste.

SUMMARY OF THE INVENTION

Cotton textile waste from fabric has been found to be a promising biomass for the production of bioethanol as a renewable fuel source. According to this disclosure, cotton textiles, such as "trash" feedstock in terms of end-of-life-cotton textiles, may be used to produce sugar without the same kinds of harsh pretreatments used for other biomasses, such as corn, grass sources, or wood. It is known that cotton has higher crystallinity [than such other biomasses], which makes it challenging to obtain very high yields of sugar. Yet, despite having higher crystallinity, cotton in the form of cotton textiles can be used to obtain high yields of sugar.

The present inventors have discovered a process for production of sugar from a cotton textile waste fabric. The process for production of sugar from a cotton textile waste fabric begins with a mild acid pretreatment step to swell the cellulose structure and permit accessibility of enzyme, followed by enzymatic degradation or hydrolysis (saccharification) of cellulose to produce sugars (e.g., glucose). No harsh pretreatment occurs. Rather, the cotton-containing textile is pretreated with a mild acid, which turns into buffer for hydrolysis enzyme—wherein buffered pH helps maintain efficacy of the enzyme. Additionally, no rinsing or neutralization or recovery or reconstitution of strong acids or bases or solvents is needed.

According to the disclosure, a process for production of sugar from a cotton-containing textile comprises:
  a. Optionally mechanically pretreating the cotton-containing textile;
  b. pretreating the cotton-containing textile with an acid pretreatment at elevated temperature to form a cotton slurry;
  c. cooling the cotton slurry from (b);
  d. adding a base to the slurry from (c);
  e. adding at least one additional acid to the cotton slurry to form a buffer in situ;
  f. adding at least one hydrolysis enzyme to the buffered cotton slurry to initiate enzymatic hydrolysis of the slurry; and
  g. optionally filtering the slurry from (f) to separate hydrolysate from cotton residue.

BRIEF DESCRIPTION OF THE FIGURES

The patent or application file contains at least one drawing executed in color. Copies of this patent or patent application

DETAILED DESCRIPTION OF THE INVENTION

Figure 1:
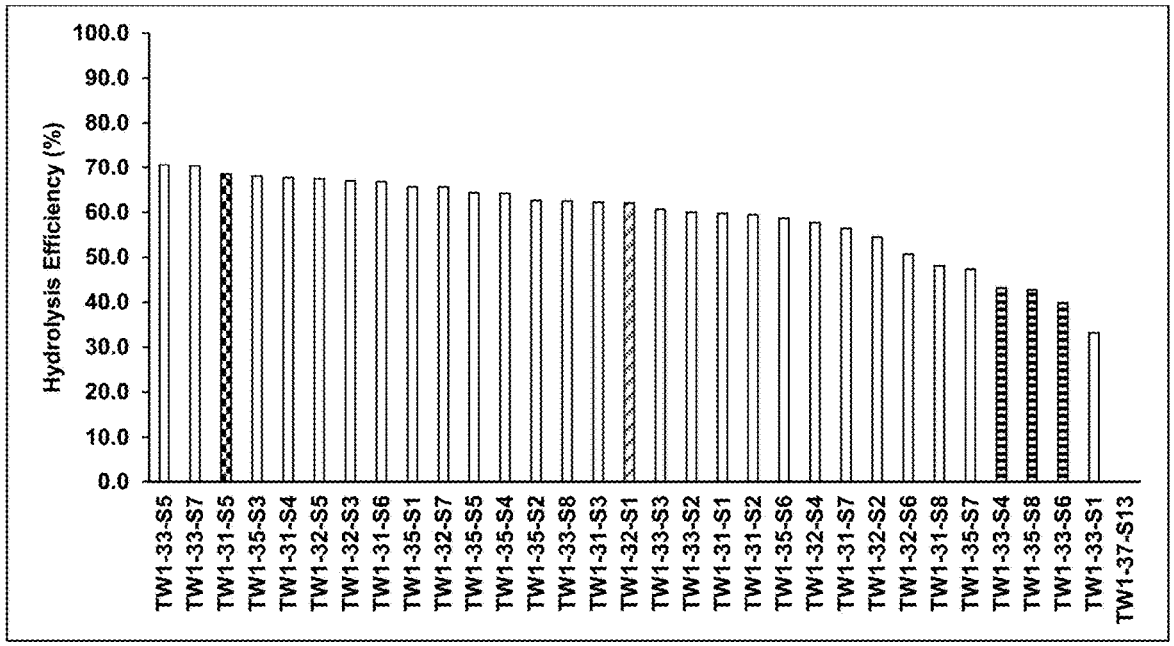
FIG. 1 shows hydrolysis efficiencies determined for each of 32 cotton textile waste samples based on Cotton Residue analysis method. 100% cotton polyester samples are shown in black-outlined/no-fill columns, cotton/polyester blend samples are shown in horizontally striped columns, cotton/viscose/nylon blend sample is shown in the checkboard-column, and content-not-identified sample is shown in the upward diagonally striped column.

The processes of the present disclosure obtain high sugar yields from cotton-containing textiles without the need for harsh pretreatment, neutralization, or rinsing steps.

According to the disclosure, a process for production of sugar from a cotton-containing textile comprises, consists essentially of, or consists of:
a. optionally mechanically pretreating the cotton-containing textile, wherein mechanical pretreatment comprises, consists essentially of, or consists of breaking down the cotton-containing textile;
b. pretreating the cotton-containing textile with an acid pretreatment at elevated temperature to form a cotton slurry;
c. cooling the cotton slurry from (b);
d. adding at least one base to the slurry from (c);
e. adding at least one additional acid to the cotton slurry to form a buffer in situ;
f. adding at least one hydrolysis enzyme to the buffered cotton slurry to initiate enzymatic hydrolysis of the slurry; and
g. optionally filtering the slurry from (f) to separate hydrolysate from cotton residue.

In a first embodiment, a process for the production of sugar from a cotton-containing textile, comprises, consists essentially of, or consists of:
a. optionally mechanically pretreating the cotton-containing textile, wherein mechanical pretreatment comprises, consists essentially of, or consists of breaking down the cotton-containing textile;
b. pretreating the cotton-containing textile with an acid pretreatment at elevated temperature to form a cotton slurry;
c. cooling the cotton slurry from (b);
d. adding at least one base to the slurry from (c);
e. adding at least one additional acid to the slurry from (d) to form a buffer in situ;
f. adding at least one hydrolysis enzyme to the buffered slurry from (e) to initiate enzymatic hydrolysis of the slurry; and
g. filtering the slurry from (f) to separate hydrolysate from residual cotton powder; and
h. fermenting the hydrolysate from (g) to form ethanol, or
g'. fermenting the slurry from (f) to form ethanol.

In an embodiment, a cotton-containing textile comprises cotton and cotton-blend garments, including, but not limited to, cotton-polyester blend garments.

In an embodiment, step (a) comprises, consists essentially of, or consists of mechanical pretreatment, which comprises, consists essentially of, or consists of breaking down the cotton-containing textile by conventional methods such as, but not limited to, grinding, shredding, cutting, chopping, or garneting. Mechanical pretreatment effectively physically breaks down the textile into smaller components and/or increases the surface area of the textile components and/or reduces crystallinity of the textile aiding in subsequent hydrolysis. In an embodiment, mechanical pretreatment comprises grinding the cotton-containing textile into a powder, wherein average particle size of the powder is between about 0.10 mm and about 2.0 mm. In another embodiment, the average particle size of the powder is between about 0.15 mm and about 1.60 mm. In another embodiment, the average particle size of the powder is between about 0.20 mm and about 1.5 mm. In another embodiment, the average particle size of the powder is less than about 2.0 mm. In another embodiment, the average particle size of the powder is less than about 1.70 mm.

The process of the disclosure may be also used for a cotton-containing textile that is already mechanically pretreated. In an embodiment, the process of the disclosure may be used for a cotton-containing textile that is already ground, shredded, cut, chopped, or garneted, for example. In an embodiment, the process of the disclosure may be used for a cotton-containing textile that is already in the form of a powder. In an embodiment, a process for the production of sugar from a mechanically pretreated cotton-containing textile, comprises, consists essentially of, or consists of:
b. pretreating the mechanically pretreated cotton-containing textile with an acid pretreatment at elevated temperature to form a cotton slurry,
c. cooling the cotton slurry from (b),
d. adding at least one base to the slurry from (c),
e. adding at least one additional acid to the slurry from (d) to form a buffer in situ,
f. adding at least one hydrolysis enzyme to the buffered slurry from (e) to initiate enzymatic hydrolysis of the slurry, and
g. filtering the slurry from (d) to separate hydrolysate from residual cotton powder
h. fermenting the residual cotton powder from (e) to form ethanol,
or
g'. fermenting the slurry from (e) to form ethanol.

In an embodiment, if the process of the disclosure is used for a cotton-containing textile that is already in the form of a powder, an average particle size of the cotton-containing textile powder may be between about 0.10 mm and about 2.0 mm. In another embodiment, the average particle size of the powder is between about 0.15 mm and about 1.60 mm. In another embodiment, the average particle size of the powder is between about 0.20 mm and about 1.5 mm. In another embodiment, the average particle size of the powder is less than about 2.0 mm. In another embodiment, the average particle size of the powder is less than about 1.70 mm.

In an embodiment, step (b) comprises, consists essentially of, or consists of pretreating the cotton-containing textile (or mechanically pretreated cotton-containing textile, if step (a) is performed) with an acid pretreatment at elevated temperature to form a cotton slurry. In an embodiment, the acid pretreatment comprises at least one acid. In an embodiment, the at least one acid comprises, consists essentially of, or consists of a weak acid. Examples of weak acids include, but are not limited to, phosphoric acid, citric acid, nitrous acid, lactic acid, benzoic acid, acetic acid, and carbonic acid. In an embodiment, in contrast to strong acids, the weak acids are acids known to not completely dissociate in water. In another embodiment, the at least one acid used in the acid pretreatment comprises, consists essentially of, or consists of phosphoric acid. In an embodiment, the concentration of the at least one acid in step (b) is between about 0.01 M and about 0.5 M, optionally between about 0.10 M and about 0.25 M, optionally between about 0.15 M and about 0.20 M.

In an embodiment, in step (b), the at least one acid is added to the powder at a liquor ratio in a range from about 2:1 to about 12:1, optionally in a range from about 4:1 to about 10:1, optionally at about 6:1.

In an embodiment, step (b) does not comprise addition of a base—i.e., a base is not used in pretreating the cotton-containing textile. In an embodiment, step (b) does not comprise a pretreatment that requires neutralization from use of a strong acid or base, recovery of any solvent or pretreatment aids, or rinsing steps necessitated from a pretreatment that requires components to be removed before hydrolysis and/or fermentation.

In an embodiment, the elevated temperature in step (b) is in a range from about 240° F. to about 410° F., optionally in a range from about 250° F. to about 280° F., optionally in a range from about 260° F. to about 270° F., optionally at about 265° F. Heating time in step (b) is in a range from about 0.5 to about 5 hours, optionally from about 1 to about 3 hours, optionally about 2 hours. Agitators may optionally be added to the slurry to enhance internal mixing of the slurry. Due to the acid pretreatment, the resulting slurry has a much lowered viscosity.

In an embodiment, step (c) comprises, consists essentially of, or consists of cooling the slurry to a temperature in a range from about 120° F. to about 160° F., optionally in a range from about 130° to about 150° F., optionally at about 140° F.

In an embodiment, step (d) comprises, consists essentially of, or consists of adding at least one base to the slurry from (c) and optionally agitating the slurry. In an embodiment, the at least one base comprises, consists essentially of, or consists of a strong base. Examples of strong bases include, but are not limited to, potassium hydroxide, sodium hydroxide, barium hydroxide, cesium hydroxide, strontium hydroxide, lithium hydroxide, and rubidium hydroxide. In another embodiment, the at least one strong base used in step (d) comprises, consists essentially of, or consists of sodium hydroxide. In an embodiment, the concentration of sodium hydroxide is in a range from about 0.01 M to about 0.5 M. In an embodiment, the concentration of sodium hydroxide is sufficient to effectively neutralize the acid previously added.

In an embodiment, the presence of sodium hydroxide neutralizes phosphoric acid to form sodium phosphate in situ. The slurry is then optionally agitated, optionally between 1 and 120 minutes, and at a temperature in a range from about 120° F. to about 160° F., optionally in a range from about 130° to about 150° F., optionally at about 140° F.

In an embodiment, step (e) comprises, consists essentially of, or consists of adding at least one additional acid to the cotton slurry from step (d) to form a buffer in situ and optionally agitating the slurry. In an embodiment, the at least one additional acid used in step (e) comprises, consists essentially of, or consists of a weak acid. Examples of weak acids include, but are not limited to, phosphoric acid, citric acid, nitrous acid, lactic acid, benzoic acid, acetic acid, and carbonic acid. In an embodiment, the weak acids do not completely dissociate in water. In another embodiment, the at least one additional acid used in step (e) comprises, consists essentially of, or consists of citric acid. In an embodiment, citric acid from step (e) forms a buffer with sodium phosphate from step (d). A citric acid and sodium phosphate buffer is known as a McMaine buffer.

In an embodiment, the concentration of the at least one acid in step (f) is between about 0.001 M and about 1.0 M, optionally between about 0.010 M and about 0.1 M, optionally between about 0.025 M and about 0.050 M.

In an embodiment, step (f) comprises, consists essentially of, or consists of adding at least one hydrolysis enzyme to the buffered cotton slurry from (e) to initiate enzymatic hydrolysis of the slurry, and optionally agitating the slurry. Enzymatic hydrolysis is carried out utilizing a cocktail combination of cellulase and β-glucosidase. Examples of hydrolysis enzymes include, but are not limited to, CTEC3 (Cellic CTec3 by Novozymes), Novozyme 188, Cellulcast 1.5L, Spezyme-CP, cellulases (e.g., Cellulase AP3), and β-glucosidase. In an embodiment, after adding the hydrolysis cocktail, hydrolysis occurs for between about 24 and about 120 hours, optionally for between about 48 and 80 hours, optionally for about 72 hours. The slurry is optionally agitated. The temperature during hydrolysis is in a range from about 80° F. to about 140° F., optionally in a range from about 110° to about 130° F., optionally at about 120° F. In another embodiment, the temperature during hydrolysis may be about 86° F., about which temperature saccharification and fermentation may occur simultaneously.

In an embodiment, step (g) comprises, consists essentially of, or consists of filtering the slurry from (f) to separate hydrolysate from cotton residue. This filtering may be done by any conventional means known to those skilled in the art, such as, for example, those described in U.S. Pat. No. 9,540,665, which is herein incorporated by reference. The cotton residue is then dried, for example in an oven, and weighed after drying. In an embodiment, the cotton residue is dried in an oven in a range from about 120° F. to about 180° F., optionally in a range from about 140° to about 170° F., optionally at about 158° F. The drying time may optionally be at least about 2 hours, optionally in a range from about 4 to about 48 hours, optionally in a range from about 10 to about 24 hours, optionally at least about 16 hours.

In an embodiment, if filtering step (g) occurs, step (h) further comprises fermenting and saccharifying the hydrolysate from (g) to form ethanol. Alternatively, if filtering step (g) does not occur, step (g') comprises fermenting and saccharifying the slurry from (f) to form ethanol.

In another embodiment, when step (h) or (g') comprises fermenting and saccharifying the hydrolysate from (g), or when step (g') comprises fermenting and saccharifying the slurry from (f), step (f) may further comprise combining the hydrolysis enzyme with yeast.

After drying, a conversion rate (or hydrolysis efficiency) may be calculated. For example, after drying, the cotton residue may be weighed at time=0 minutes and time≥15 minutes. The conversion rate is then calculated based on the amount of cotton added and the weight of residue at time≥15 minutes. In an embodiment, HPLC and RIDA® Cube are analysis methods that may be used to measure glucose concentration of the solution to calculate the hydrolysis efficiency.

In an embodiment, the hydrolysis efficiency is at least about 10%, at least about 20%, at least about 30%, at least about 40%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, or at least about 80%. The hydrolysis efficiency may be determined in a manner known to one of skill in the art. Exemplary analysis methods include Cotton Residue, HPLC, and RIDA® Cube. In an embodiment, hydrolysis efficiency is determined using the RIDA® Cube method.

In an embodiment, the process for production of sugar from a cotton-containing textile does not comprise a pretreatment that requires neutralization from use of a strong acid or base, recovery of any solvent or pretreatment aids, or rinsing steps necessitated from a pretreatment that requires components to be removed before hydrolysis and/or fermentation.

In an embodiment, the temperature, concentration, and time values provided above are representative and not restrictive. For example, the pH and buffering capacity may be adjusted by adjusting the concentration of the acids and/or base(s). Similarly, the pretreatment time and temperature may be shortened or extended. Finally, hydrolysis time may be shortened or extended, thus increasing or lowering the amount of enzyme needed. It is also possible to adjust the solids of the process (i.e., the liquor ratio).

EXAMPLES

A cotton containing textile is cut and ground into a powder using a Thomas Wiley Mini-Mill grinder. The cotton powder is pretreated with 18.22 g/L phosphoric acid at a 6:1 liquor ratio at 265° F. for 2 h in a Roaches Pyrotec dyeing machine. Ball bearings are added to enhance internal mixing of the cotton slurry. The acid pretreatment creates a homogenous cotton slurry with much lowered viscosity. The pretreated cotton slurries are cooled to 140° F., and to each slurry, 8.92 g/L of NaOH is added. The caustic effectively converts the phosphoric acid to form sodium phosphate in situ. The slurry containing the pretreated cotton, phosphoric acid and sodium hydroxide is circulated for 15 min at 140° F. in the Roaches Pyrotec dyeing machine to form the sodium phosphate.

Next, 8.50 g/L citric acid is added to each slurry, and the slurry containing the phosphoric acid, sodium hydroxide, and citric acid is circulated again for 15 min at 140° F. in the Roaches Pyrotec dyeing machine. The combination of the citric acid and sodium phosphate forms a buffer in the pretreated cotton slurry. Next, 10% owg of enzyme cocktail (10:1 liquor) is added to each slurry, and hydrolysis occurs for 72 h at 120° F.

Table A of the disclosure sets forth 32 cotton textile waste samples and includes percentage cotton, where applicable.

TABLE A

Cotton textile waste hydrolyzed

| Sample | Garment Description |
| --- | --- |
| TW1-31-S1 | Chaps Black, White, and Blue Striped Polo Shirt (100% Cotton) |
| TW1-31-S2 | Brown King Size Sheets (100% Egyptian Cotton) |
| TW1-31-S3 | Kirkland White and Blue Checkered Dress Shirt (100% Extra Long Staple Cotton/Non-Iron Resin Finish) |
| TW1-31-S4 | Fruit of the Loom Navy Blue T-Shirt (100% Cotton) |
| TW1-31-S5 | Merona Red Sweater with Jewel Embroidery (53% Cotton/40% Rayon/7% Nylon) |
| TW1-31-S6 | Ralph Lauren Classic Fit White Dress Shirt w/Red and Blue Checkers (100% Cotton) |
| TW1-31-S7 | Nautica Red, White, and Blue Checkered Dress Shirt (100% Cotton) |
| TW1-31-S8 | Hanes Black Beefy-Tee Long Sleeve Shirt (100% Preshrunk Cotton) |
| TW1-32-S1 | Tommy Hilfiger Red, White, and Blue Long Sleeve Shirt (no label or label faded) |
| TW1-32-S2 | Chaps Ralph Lauren Red, White, and Blue Long Sleeve Shirt (100% Cotton) |
| TW1-32-S3 | Old Navy Red, White, and Blue Long Sleeve Shirt (100% Cotton) |
| TW1-32-S4 | Hanes White T-Shirt (100% Cotton) |
| TW1-32-S5 | Ralph Lauren Blue, Green, Red, and White Striped Dress Shirt (100% Cotton) |
| TW1-32-S6 | Ralph Lauren Blue and White Striped Dress Shirt (100% Cotton) |
| TW1-32-S7 | Ralph Lauren Pink, Green, Orange, Black, and White Dress Shirt (100% Cotton) |
| TW1-33-S1 | Black Croft and Barrow Polo Shirt (100% Cotton/Easy Care) |
| TW1-33-S2 | Haggar Off-White Khaki Pant (100% Cotton/Resin Finish) |
| TW1-33-S3 | Green/Blue Pin Stripe Croft and Barrow Dress Shirt (100% Cotton/Resin Finish) |
| TW1-33-S4 | White George Polo Shirt (60% Cotton/40% Polyester) |
| TW1-33-S5 | Blue Tommy Hilfiger Dress Shirt (100% Cotton) |
| TW1-33-S6 | Blue/White Chaps Dress Shirt (55% Cotton/45% Polyester/Regular Fit/Wrinkle-Free) |
| TW1-33-S7; TW1-34-S1; TW1-34-S2 | Green Faded Glory T-Shirt with Pocket (100% Cotton) (no label or label faded) |
| TW1-33-S8 | Levi's Light Blue Washed Jeans (100% Cotton/Relaxed Fit) |
| TW1-35-S1 | Urban Pipeline Light Blue Washed Jeans (with Holes) (100% Cotton/Relaxed Boot Cut) |
| TW1-35-S2 | Eddie Bauer Tan Khaki Pant (100% Cotton) |
| TW1-35-S3 | Old Navy Grey Loose Cargo Pant (100% Cotton) |
| TW1-35-S4 | Dockers Off-White Khaki Pant (100% Cotton) |

TABLE A-continued

Cotton textile waste hydrolyzed

| Sample | Garment Description |
| --- | --- |
| TW1-35-S5 | Forsyth of Canada Pin Stripe White and Blue Dress Shirt (100% Cotton/Wrinkle-Free/2 ply 80's) |
| TW1-35-S6 | Joseph & Feiss Brown Dress Shirt (100% Cotton/Non-Iron Resin Finish) |
| TW1-35-S7 | Haggar Black Khaki Pant (100% Cotton/Non-Iron Care) |
| TW1-35-S8 | Chaps Blue and Tan Checkered Dress Shirt (60% Cotton/40% Polyester/Easy Care) |
| TW1-37-S13 | Arnold Palmer Pink and White Striped Polo Shirt (100% Polyester) |

Figure 2:
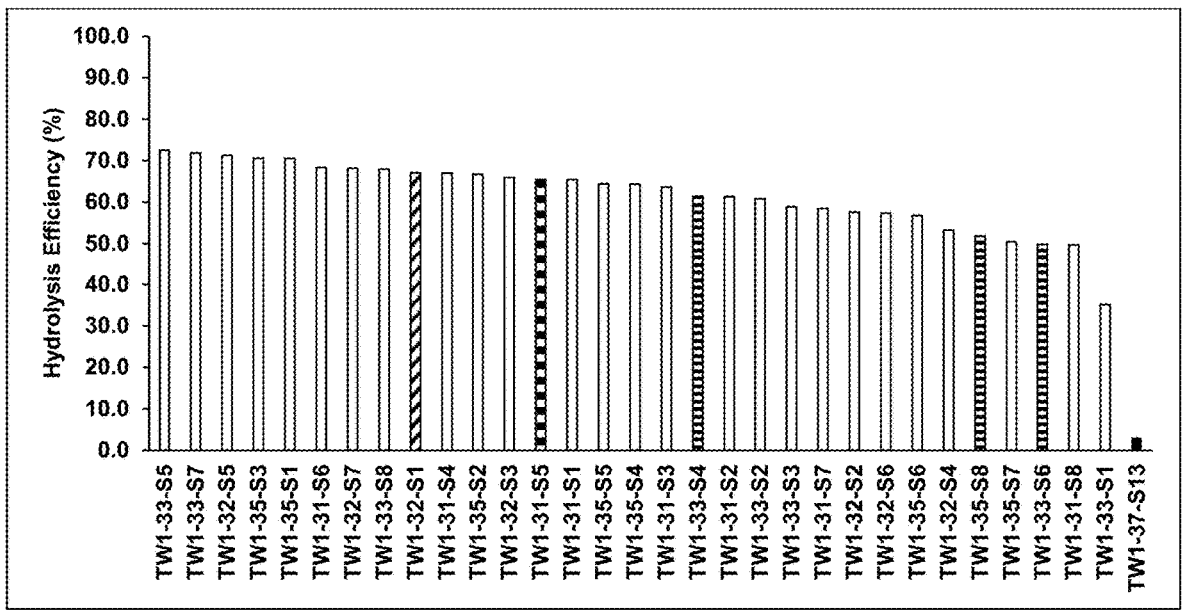
FIG. 2 shows efficiencies determined for each of 32 cotton textile waste samples based on HPLC analysis method. 100% cotton polyester samples are shown in black-outlined/no-fill columns, cotton/polyester blend samples are shown in horizontally striped columns, cotton/viscose/nylon blend sample is shown in the checkboard-column, content-not-identified sample is shown in the upward diagonally striped column, and 100% polyester sample is shown in the black-filled column.
Figure 3:
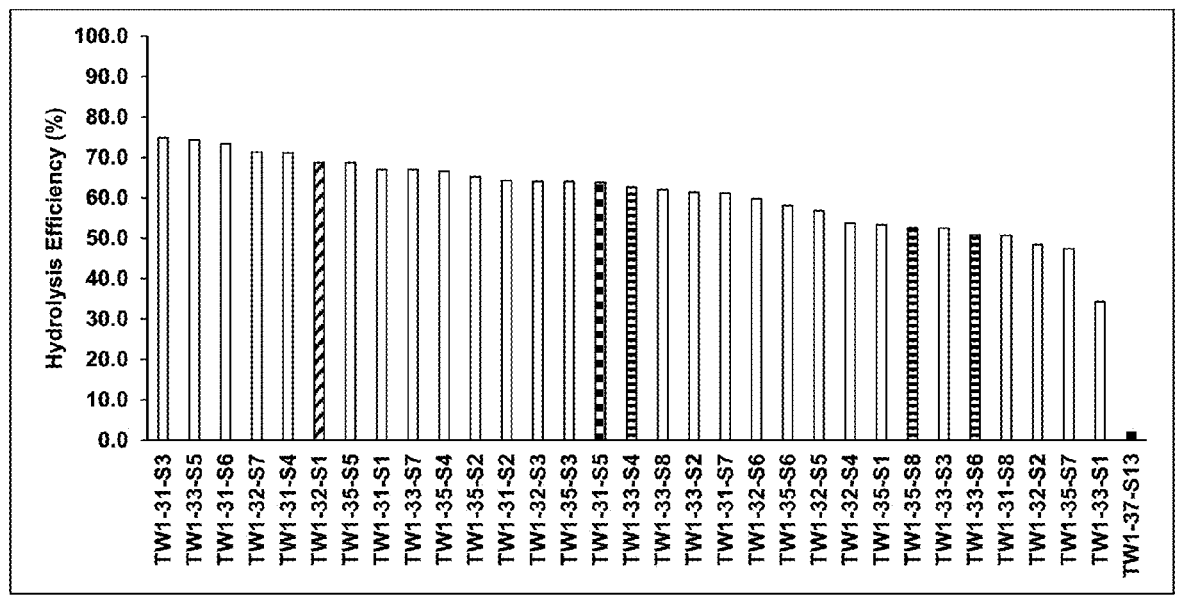
FIG. 3 shows hydrolysis efficiencies determined for each of 32 cotton textile waste samples based on RIDA® Cube analysis method. 100% cotton polyester samples are shown in black-outlined/no-fill columns, cotton/polyester blend samples are shown in horizontally striped columns, cotton/viscose/nylon blend sample is shown in the checkboard-column, content-not-identified sample is shown in the upward diagonally striped column, and 100% polyester sample is shown in the black-filled column.

The hydrolysis efficiencies of these 32 cotton textile waste samples using the same conditions (i.e., 18.22 g/L $H_3PO_4$, 2 hours, 265° F. pretreatment; 10% enzyme cocktail enzymatic hydrolysis, 72 hours, 120° F.) were evaluated. FIGS. 1-3 show the hydrolysis efficiencies determined for each sample based on the Cotton Residue, HPLC, and RIDA® Cube analysis methods. The highest values observed were ca. 73-75% (RIDA® Cube method). TW1-33-S5, a 100% cotton dress shirt, was among the top-2 samples with the highest hydrolysis efficiencies seen across all three analysis methods (i.e., 70.6, 72.5 and 74.3% for Cotton Residue, HPLC, and RIDA® Cube methods, respectively), while TW1-37-13, a 100% polyester shirt, displayed the lowest values seen based on HPLC and RIDA® Cube methods (3.0 and 2.2%, respectively). The latter result was anticipated due to the lack of hydrolysable bonds in polyester by cellulases and other enzymes present in the enzyme cocktail. The low sugar levels detected were most likely due to the presence of reducing sugars from the enzymes. The next lowest values seen across all three analysis methods were for TW1-33-S1, a black 100% cotton shirt (i.e., 33.2, 35.2 and 34.3% for Cotton Residue, HPLC, and RIDA® Cube methods, respectively). The values seen among other all-black 100% cotton waste textile samples were also low (ca. 47-51%). However, the values seen among other dyed 100% cotton waste textile samples in many cases exceeded this range, suggesting the presence of the high concentration of black dye in these samples may influence hydrolysis.

Of the thirty-two samples analyzed, twenty-six were 100% cotton. The average hydrolysis efficiencies for the 100% cotton samples were 60.5, 62.3, and 61.2% for Cotton Residue, HPLC, and RIDA® Cube methods, respectively. Four blends were analyzed (either cotton/polyester or cotton/viscose/nylon), and the treatment was effective for the hydrolysis of each (ca. 40-69%). It should be understood that the Cotton Residue method gave considerably lower efficiencies for the blends as compared to HPLC and RIDA® Cube. Additionally, efficiencies are given based on the total weight of the sample. In reality, nearly complete conversion of the theoretical amount of glucose in the blends was obtained for the cotton/polyester blends. Similarly, TW1-31-S5, a red 53/40/7 cotton/viscose/nylon sweater, displayed the highest efficiencies across all three analysis methods (i.e., 68.5, 65.5 and 63.8% for Cotton Residue, HPLC, and RIDA® Cube methods, respectively), and its efficiency was comparable to multiple 100% cotton waste textile samples studied. This is attributed to the blend because the cellulose content (from both cotton and viscose) was the highest, i.e., 93% theoretical glucose. However, the efficiency of the theoretical glucose is lower than the cotton/polyester blends. It is assumed this is due to higher concentrations of enzyme with lowering the blend percentage of cotton, even though the amount of enzyme is based on sample size and kept the same for all experiments.

Figure 4:
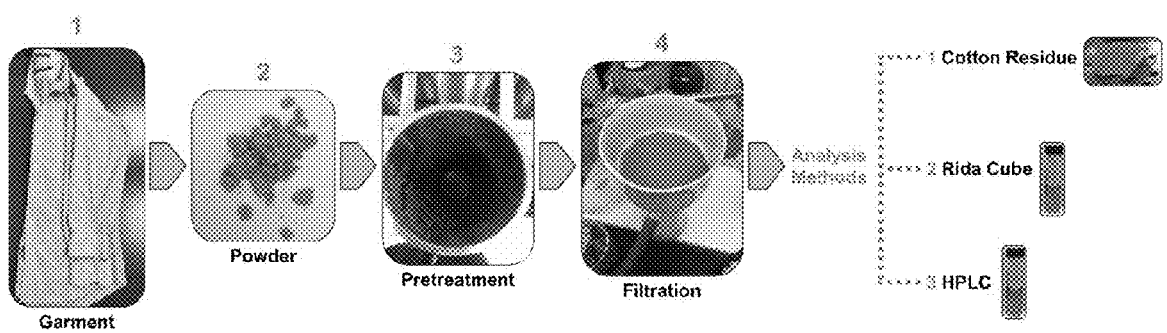
FIG. 4 shows the stages of a 100% cotton waste sample, beginning with its initial garment form, that was hydrolyzed.

FIG. 4 shows the stages of a 100% cotton waste sample (TW1-31-S3) that was hydrolyzed, beginning with its initial garment form: (1) initial garment form, (2) milled powder form, (3) condition after acid pretreatment, (4) filtered form (top layer: cotton residue, filtrate: hydrolysate). For this particular sample, a maximum hydrolysis efficiency of 74.9% was achieved (RIDA® Cube method).

Figure 5:
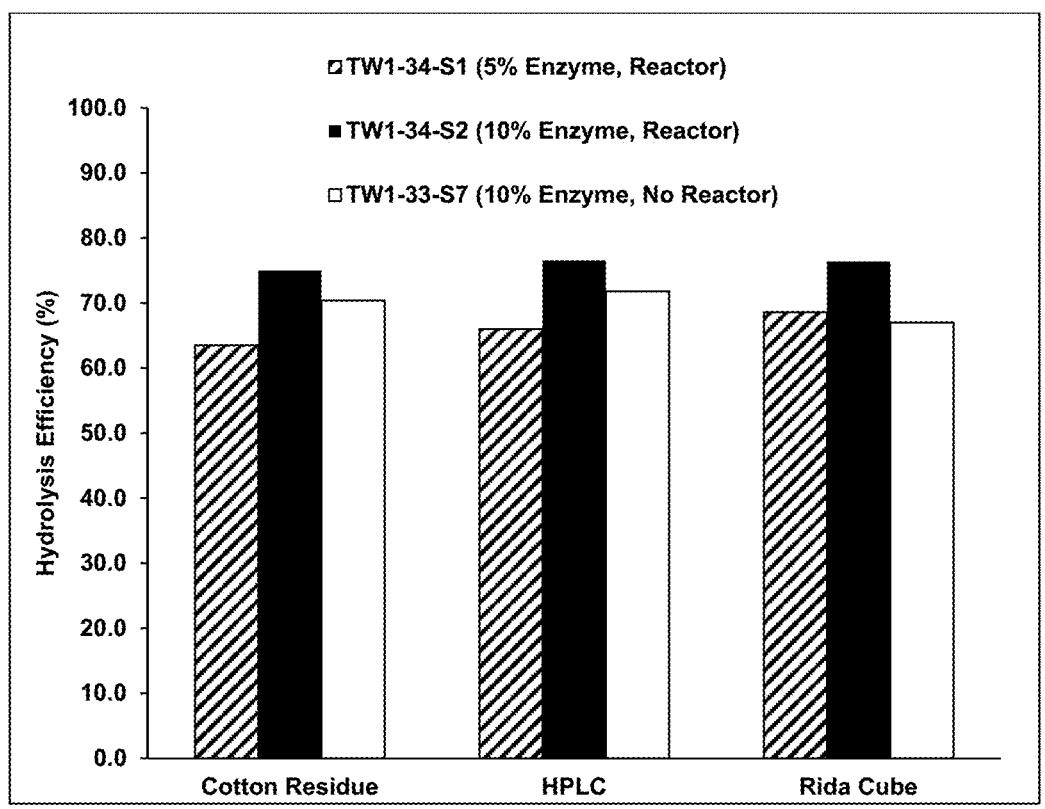
FIG. 5 shows hydrolysis efficiencies for a 100% cotton T-shirt hydrolyzed (all methods).

A 100% cotton T-shirt was exposed to a hydrolysis treatment after using a high pressure and temperature reactor pretreatment and 5% or 10% owg enzyme cocktail, TW1-34-S1 and TW1-34-S2, respectively. The cotton shirt was selected, because when hydrolyzed during preliminary studies, hydrolysis efficiencies between ca. 71-79% across all three analysis methods (Cotton Residue, HPLC, and RIDA® Cube) were achieved. FIG. 5 shows the comparison of the results from hydrolyzing TW1-34-S1 and TW1-34-S2.

FIG. 5 also shows the results from the hydrolysis of TW1-33-S7, a sample from the same cotton T-shirt that was hydrolyzed without the use of a high pressure and temperature reactor and using 10% owg enzyme cocktail. The results show that the use of the reactor aided in an increase in hydrolysis efficiency. These results show it is possible to cut the enzyme dose by half from 10% to 5% on a garment and increase the pretreatment temperature and obtain almost comparable levels of hydrolysis as the 10% enzyme dose at a lower pretreatment temperature.

Table B of the disclosure sets forth the hydrolysis efficiencies (in %) observed in the samples of Table A for each of the analysis methods used: Cotton Residue, HPLC, and RIDA® Cube.

TABLE B

Overview of hydrolysis experimental work and results

| Sample | Pretreatment Conditions | pH Before Addition of enzyme cocktail | Hydrolysis Conditions | pH After Hydrolysis | Hydrolysis Efficiency (%, Based on Method) | | |
| --- | --- | --- | --- | --- | --- | --- | --- |
| | | | | | Cotton Residue | HPLC | RIDA® Cube |
| TW1-31-S1 | 18.22 g/L | 5.36 | 10% enzyme | 5.13 | 59.8 | 65.5 | 67.0 |
| TW1-31-S2 | $H_3PO_4$ | 5.62 | cocktail | 5.34 | 59.5 | 61.3 | 64.3 |

TABLE B-continued

Overview of hydrolysis experimental work and results

| Sample | Pretreatment Conditions | pH Before Addition of enzyme cocktail | Hydrolysis Conditions | pH After Hydrolysis | Hydrolysis Efficiency (%, Based on Method) | | |
|---|---|---|---|---|---|---|---|
| | | | | | Cotton Residue | HPLC | RIDA® Cube |
| TW1-31-S3 | (6:1 liquor ratio), 265° F., 2 h | 5.54 | (10:1 liquor ratio), 120° F., 72 h) | 5.42 | 62.2 | 63.6 | 74.9 |
| TW1-31-S4 | | 5.37 | | 5.14 | 67.7 | 67.0 | 71.1 |
| TW1-31-S5 | | 5.49 | | 5.12 | 68.5 | 65.5 | 63.8 |
| TW1-31-S6 | | 5.52 | | 5.26 | 66.8 | 68.4 | 73.4 |
| TW1-31-S7 | | 5.47 | | 5.30 | 56.4 | 58.5 | 61.2 |
| TW1-31-S8 | | 5.49 | | 5.13 | 48.1 | 49.7 | 50.7 |
| TW1-32-S1 | | 5.51 | | 4.98 | 62.0 | 67.1 | 68.7 |
| TW1-32-S2 | | 5.53 | | 5.04 | 54.5 | 57.6 | 48.4 |
| TW1-32-S3 | | 5.28 | | 4.85 | 67.0 | 65.9 | 64.0 |
| TW1-32-S4 | | 5.51 | | 5.23 | 57.7 | 53.3 | 53.7 |
| TW1-32-S5 | | 5.42 | | 5.10 | 67.5 | 71.3 | 56.8 |
| TW1-32-S6 | | 5.03 | | 5.11 | 50.7 | 57.4 | 59.8 |
| TW1-32-S7 | | 5.45 | | 5.10 | 65.6 | 68.2 | 71.3 |
| TW1-33-S1 | | 5.30 | | 5.04 | 33.2 | 35.2 | 34.3 |
| TW1-33-S2 | | 5.53 | | 5.40 | 60.0 | 60.8 | 61.4 |
| TW1-33-S3 | | 5.45 | | 5.49 | 60.7 | 58.9 | 52.5 |
| TW1-33-S4 | | 5.32 | | 5.28 | 43.2 | 61.4 | 62.7 |
| TW1-33-S5 | | 5.33 | | 5.15 | 70.6 | 72.5 | 74.3 |
| TW1-33-S6 | | 5.30 | | 5.23 | 39.9 | 49.8 | 50.8 |
| TW1-33-S7 | | 5.32 | | 5.16 | 70.4 | 71.8 | 67.0 |
| TW1-33-S8 | | 5.15 | | 5.08 | 62.5 | 67.9 | 62.0 |
| TW1-35-S1 | | 5.38 | | 4.90 | 65.7 | 70.6 | 53.3 |
| TW1-35-S2 | | 5.40 | | 5.18 | 62.6 | 66.7 | 65.2 |
| TW1-35-S3 | | 5.36 | | 5.21 | 68.1 | 70.6 | 64.0 |
| TW1-35-S4 | | 5.47 | | 5.40 | 64.2 | 64.4 | 66.6 |
| TW1-35-S5 | | 5.44 | | 5.34 | 64.3 | 64.4 | 68.7 |
| TW1-35-S6 | | 5.54 | | 5.51 | 58.7 | 56.8 | 58.1 |
| TW1-35-S7 | | 5.31 | | 5.21 | 47.4 | 50.5 | 47.4 |
| TW1-35-S8 | | 5.39 | | 5.25 | 42.8 | 51.8 | 52.6 |
| TW1-37-S13 | | 5.46 | | 5.40 | — | 3.0 | 2.2 |
| TW1-34-S1 | 18.22 g/L H₃PO₄ (6:1 liquor ratio), 265° F., 3 h/ | 5.40 | 5% enzyme cocktail (10:1 liquor ratio), 120° F., 72 h) | 5.27 | 63.51 | 66.00 | 68.60 |
| TW1-34-S2 | 338° F., 1.5 h | 5.36 | 10% enzyme cocktail (10:1 liquor ratio), 120° F., 72 h) | 5.26 | 75.00 | 76.54 | 76.40 |

It is apparent that embodiments other than those expressly described herein come within the spirit and scope of the present claims. Accordingly, the present invention is not defined by the above description, but is to be accorded the full scope of the claims so as to embrace any and all equivalent compositions and methods.

The invention claimed is:

1. A process for production of sugar from a cotton-containing textile comprising:
   a. mechanically pretreating the cotton-containing textile, wherein the mechanical pretreatment comprises breaking down the cotton-containing textile;
   b. pretreating the mechanically pretreated cotton-containing textile with a first weak acid pretreatment at elevated temperature to form a cotton slurry, wherein the elevated temperature is in a range of about 240° F. to about 410° F.;
   c. cooling the cotton slurry from (b);
   d. adding a base to the slurry from (c);
   e. adding a second weak acid to the slurry from (d) to form a buffer in situ,
   f. adding a hydrolysis enzyme to the buffered slurry from (e) to initiate enzymatic hydrolysis of the slurry; and
   g. filtering the slurry from (f) to separate hydrolysate from cotton-containing textile residue,
   with the proviso that the process does not comprise rinsing, neutralization, recovery or reconstitution with strong acids, bases, or solvents.

2. The process of claim 1, wherein the weak acid comprises phosphoric acid.

3. The process of claim 1, wherein the base comprises a strong base.

4. The process of claim 1, wherein the base comprises sodium hydroxide.

5. The process of claim 1, wherein the hydrolysis enzyme is a combination of cellulase and β-glucosidase.

6. The process of claim 1, wherein the elevated temperature in step (b) is in a range from about 250° F. to about 280° F.

7. The process of claim 1, wherein in (a), said breaking down comprises grinding, shredding, cutting, chopping, or garneting.

8. The process of claim 1, wherein in (a), said breaking down comprises grinding.

9. The process of claim 1, wherein hydrolysis efficiency is at least 50%.

10. The process of claim 1, wherein hydrolysis efficiency is at least 60%.

11. The process of claim 1, wherein hydrolysis efficiency is at least 65%.

12. The process of claim 1, wherein hydrolysis efficiency is at least 70%.

13. The process of claim 1, wherein the first weak acid is phosphoric acid, citric acid, nitrous acid, lactic acid, benzoic acid, acetic acid, or carbonic acid.

14. The process of claim 1, wherein the second weak acid is phosphoric acid, citric acid, nitrous acid, lactic acid, benzoic acid, acetic acid, or carbonic acid.

15. The process of claim 1, wherein the second weak acid is citric acid.

16. The process of claim 3, wherein the strong base is potassium hydroxide, sodium hydroxide, barium hydroxide, cesium hydroxide, strontium hydroxide, lithium hydroxide, or rubidium hydroxide.

\* \* \* \* \*